(12) United States Patent
Stroud et al.

(10) Patent No.: US 8,979,987 B1
(45) Date of Patent: Mar. 17, 2015

(54) BLUE DYE AND METHODS OF MANUFACTURE AND USE THEREOF

(71) Applicant: Viscot Medical, LLC., East Hanover, NJ (US)

(72) Inventors: Eric Stroud, Oak Ridge, NJ (US); Gary J. Pieringer, Shrewsbury, NJ (US)

(73) Assignee: Viscot Medical, LLC, East Hanover, NJ (US)

( * ) Notice: Subject to any disclaimer, the term of this patent is extended or adjusted under 35 U.S.C. 154(b) by 70 days.

(21) Appl. No.: 13/857,632

(22) Filed: Apr. 5, 2013

Related U.S. Application Data

(60) Provisional application No. 61/621,183, filed on Apr. 6, 2012.

(51) Int. Cl.
   C09D 11/17     (2014.01)
   C09B 35/16     (2006.01)
   A61B 17/00     (2006.01)
   A61B 19/00     (2006.01)

(52) U.S. Cl.
   CPC ..................... *A61B 19/54* (2013.01)
   USPC ............... 106/31.03; 106/31.52; 534/824; 534/825; 534/826; 606/1; 606/116; 604/2

(58) Field of Classification Search
   CPC ........ C09D 11/17; C09B 35/16; A61B 17/00; A61M 35/00
   USPC ............ 106/31.03, 31.52; 534/824, 825, 826; 606/1, 116; 604/2
   See application file for complete search history.

(56) References Cited

U.S. PATENT DOCUMENTS 2,489,463 A * 11/1949 Reynolds ................ 106/31.52
2,820,783 A *  1/1958 Riat ............................ 534/826
3,259,498 A *  7/1966 Boehl et al. ............... 534/826

(Continued)

*Primary Examiner* — Helene Klemanski
(74) *Attorney, Agent, or Firm* — Moser Taboada; Alan Taboada

(57) ABSTRACT

Provided, amongst other things, are dyes of formula II:

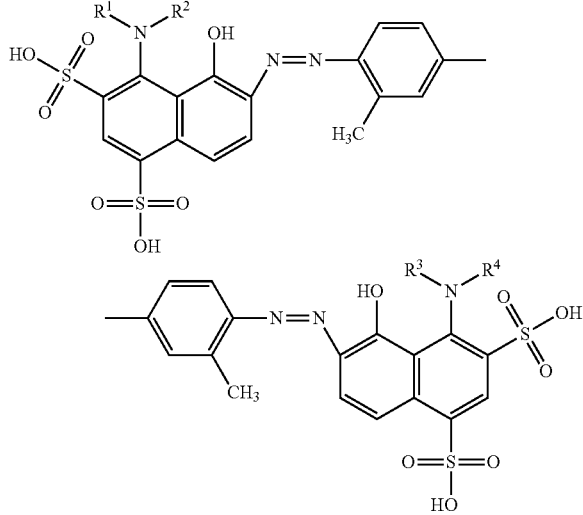

wherein $R^1$, $R^2$, $R^3$ and $R^4$ are independently H or alkyl, so long as one or more is alkyl, and salts of the compound of formula II. Methods of making, inks, surgical markers and methods of marking tissue and the like are further provided.

20 Claims, 2 Drawing Sheets

(56) References Cited

U.S. PATENT DOCUMENTS

| | | | |
|---|---|---|---|
| 4,163,012 A | * | 7/1979 | Kramer et al. ............... 534/826 |
| 4,973,672 A | * | 11/1990 | Bauer et al. ................. 534/825 |
| 7,160,377 B2 | * | 1/2007 | Zoch et al. ................. 106/31.52 |
| 2008/0269694 A1 | * | 10/2008 | Pieringer ..................... 604/218 |
| 2010/0121343 A1 | * | 5/2010 | Stroud et al. ................ 606/116 |

\* cited by examiner

BLUE DYE AND METHODS OF MANUFACTURE AND USE THEREOF

CROSS-REFERENCE TO RELATED APPLICATIONS

This application claims benefit of U.S. provisional patent application Ser. No. 61/621,183, filed Apr. 6, 2012, which is herein incorporated by reference in its entirety.

FIELD

The present application relates generally to blue dyes useful, for example, in marking inks.

BACKGROUND

One dye useful, for example, in marking inks is a salt of 3,3'-dimethylbiphenyl-4,4'-diyl)dihydrazin-2-yl-1-ylidene]bis(4-amino-5-oxo-5,6-dihydronaphthalene-1,3-disulfonate (hereinafter referred to by CAS No. 314-13-6). Its chemical features include multiple functional groups including sulfate, hydrazo, amine and hydroxy (namely phenoxy). The hydroxy is adjacent to amine and to a nitrogen in hydrazo, such that the hydrogen of hydroxy is believed to tautomerize with one or both adjacent electron donor moieties. This tautomerization, which is duplicated at two ends of the molecule, is believed to contribute to the excellent color of CAS No. 314-13-6. As such, this compound may be used as a dye, for example, in a marking ink, used, for example, to mark patients prior to or during surgical procedures.

However, the inventors have observed that conventional marking inks, including those containing CAS No. 314-13-6, tend to rapidly lose visibility in certain applications, such as when used to mark internal tissue.

Thus, the inventors have provided embodiments of additional compounds useful, for example, in marking inks.

SUMMARY

Provided herein is a dye of formula II:

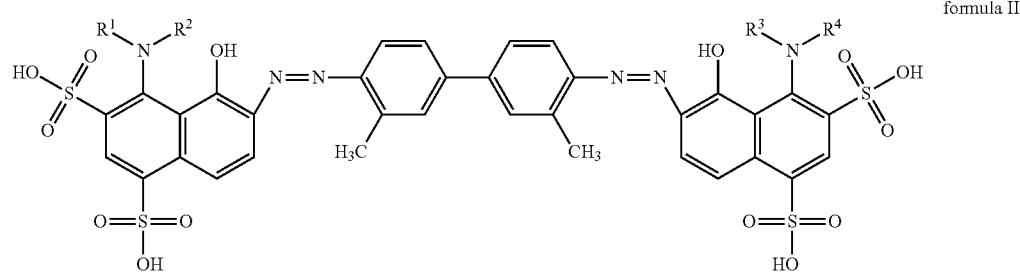

formula II wherein $R^1$, $R^2$, $R^3$ and $R^4$ are independently H or alkyl, so long as one or more is alkyl, and salts of the compound of formula II. In certain embodiments, alkyl of $R^1$, $R^2$, $R^3$ or $R^4$ is C1-C4 alkyl. In certain embodiments, one or more alkyls of $R^1$, $R^2$, $R^3$ or $R^4$ is attached via a primary carbon.

In certain embodiments, inks are provided comprising the dye. In certain embodiments, surgical markers are provided comprising the dye described herein.

In certain embodiments, an apparatus for marking patients, is provided comprising: an ink reservoir; an ink dispenser having a fluid connection to the ink reservoir to dispense the ink at a desired rate to mark a patient; and an ink disposed in the ink reservoir, the ink comprising the dye described herein.

In certain embodiments, a method of marking a patient is provided, comprising: determining a portion of a patient to be marked; and applying an ink to the patient to mark the portion of the patient, the ink comprising the dye described herein.

Other embodiments, features, and benefits, are described in more detail below.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings or incorporated structures or chemical schemes. It is to be noted, however, that the drawings, structures and schemes illustrate only illustrative embodiments of this invention and are therefore not to be considered limiting of its scope, for the invention may admit to other equally effective embodiments.

Figure 1:
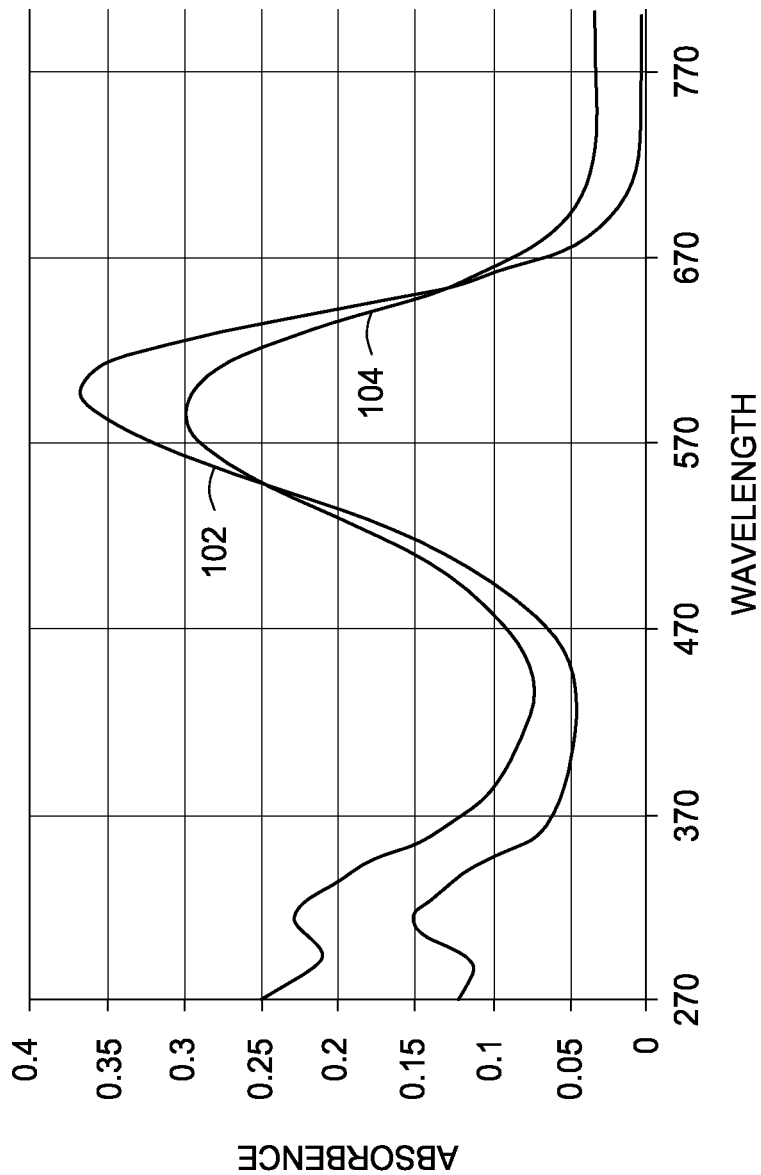
FIG. 1 shows UV/Vis spectra of CAS No. 314-13-6 and a dye in accordance with some embodiments of the present invention.

It is contemplated that elements and features of one embodiment may be beneficially incorporated in other embodiments without further recitation.

DETAILED DESCRIPTION

Salts of 3,3'-dimethylbiphenyl-4,4'-diyl)dihydrazin-2-yl-1-ylidene]bis(4-amino-5-oxo-5,6-dihydronaphthalene-1,3-disulfonate (hereinafter referred to by CAS No. 314-13-6) generally have the following formula:

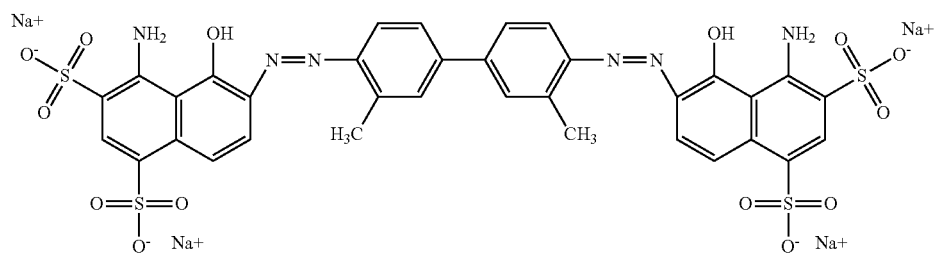

Formula I

CAS No. 314-13-6 presents numerous competing nucleophiles when reacted under basic conditions. Nonetheless, it has now been discovered that the amines can be unexpectedly alkylated without detriment to the spectroscopic properties of CAS No. 314-13-6. Moreover, it has further been discovered that dye compounds obtained in the manner disclosed herein, and inks comprising such dye compounds, may advantageously retain visibility for longer periods of time when used to mark internal tissues as compared to conventional dyes comprising unmodified CAS No. 314-13-6.

The dye compounds of the invention (i.e., the modified dye) are believed to be:

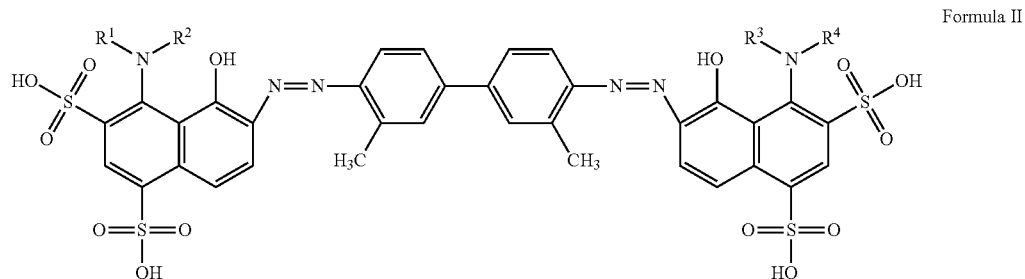

Formula II and salts thereof (e.g., acid addition salts), where $R^1$, $R^2$, $R^3$ and $R^4$ are independently H or alkyl, so long as one is alkyl. Since the dye can be used to mark biological tissue, it can be useful to use pharmaceutically acceptable salts. One sodium salt of particular interest is:

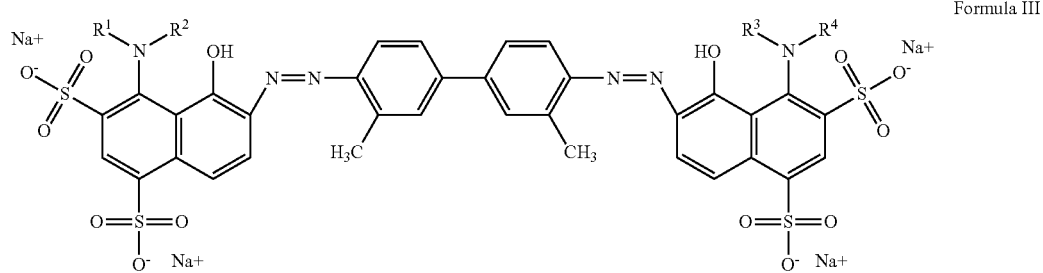

Formula III

Irrespective of the formula, one compound of the invention is the formula identified by further analytical analysis of the product of the synthesis described herein. One or more of $R^1$, $R^2$, $R^3$ and $R^4$, is preferably C1 to C4 alkyl, such as C1 to C3 or C1 to C2. In certain embodiments, one or more of $R^1$, $R^2$, $R^3$ and $R^4$ is alkyl is attached via a primary carbon. In certain embodiments, two or more of $R^1$, $R^2$, $R^3$ and $R^4$ are alkyl, or three or more, or all four.

The compound of Formula II can be synthesized (typically from a salt) via $S_n2$ reaction as follows (where $R^1$ is the central biphenyl moiety illustrated above):

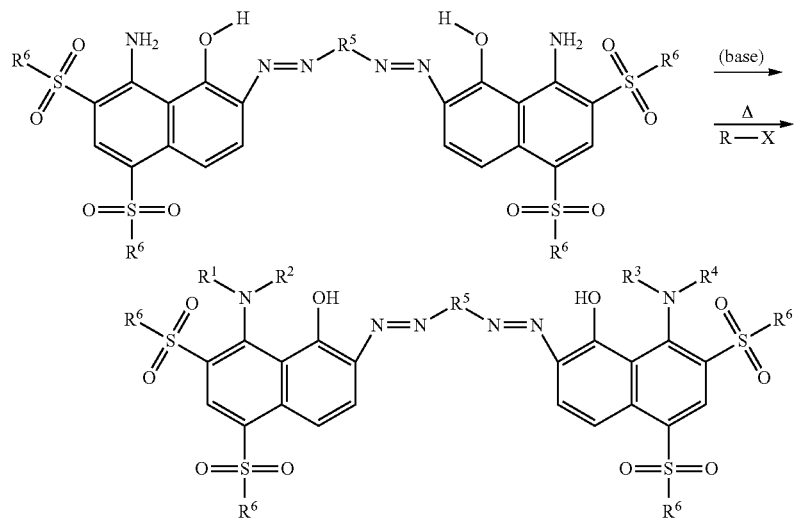

$R^6$ represents $-O^-M^+$, where $M^+$ is a cation (such as a sodium or potassium ion). The amine is represented in the base form, and the hydroxy in protonated form, but it may be that the reaction conditions can be selected to allow these titration forms to differ from what is illustrated. X is an appropriate leaving group. Preferably, X is halide such as chloride, bromide or iodide. R may be a mixture of alkyls defining alkyl(s) of $R^1$, $R^2$, $R^3$ and $R^4$, or a given such alkyl. Base is preferably added before addition of R—X, but concurrent addition is not excluded. $R^5$ is the central biphenyl moiety illustrated above. In certain embodiments, the starting material may be sufficiently in free base form to allow a useful amount of alkylation without added base.

In the synthesis, the solvent can be selected to be aprotic and relatively polar, such as tetrahydrofuran, and to sustain a reaction temperature above room temperature, but generally not extremely elevated, such as a temperature from about 40° C. to about 65° C., or from about 10° C. to about 80° C. A modest reaction temperature and patience with the resulting long reaction time are believed to be important to obtaining the desired product. Reaction times can be, for example, 4 to 10 hours.

A less than stoichiometric amount of base can be used. Base can be for example NaOH, KOH, LiOH, $C_2H_5ONa$, and the like. Typically, a greater than stoichiometric amount of R—X is used. R—X can be added after a blue color shift in the reaction mixture indicates that the phenoxide anion has formed.

The reaction can be monitored by thin layer chromatography, such as on silica plates developed with aqueous methanol. The reaction can be ended by precipitating the product with a more apolar solvent, and removing solvent and R—X by rotary evaporation (or filtration). Liquid-liquid extractions and/or additional precipitations can be used to further purify the product.

The salt form obtained from the synthesis can be exchanged to other salt forms or to the free acid as is known in the art.

The dye can be formulated into an ink by methods known in the art. For example, in some embodiments, an ink suitable for marking internal tissue may comprise about 89.5% w/w water, about 10.0% w/w modified dye, and about 0.50% w/w preservative, such as diazolidynyl urea. In some embodiments, the ink as described above may be made by slowly adding the modified dye to a container of water under moderate agitation. After mixing for 5 minutes, the preservative is slowly added and the solution is agitated for an additional 5 minutes before use. Other ink formulations and other methods of fabrication may be used.

By appropriate selection of $R^1$, $R^2$, $R^3$ and $R^4$, it is believed that one can tune solubility of the dye in different ink delivery systems, and improve adhesion and marking characteristics, especially for internal organs. By appropriate selection of $R^1$, $R^2$, $R^3$ and $R^4$, it is believed that one can potentially slow down the decolorizating (azo de-linkage) enzymatic reactions that degrade CAS No. 314-13-6 when applied to the surfaces of internal organs. For example, the inventors have observed that conventional marking inks, including those containing conventional dyes comprising CAS No. 314-13-6, tend to rapidly lose visibility when used to mark internal tissue. The inventors have discovered that inks prepared according to the teachings provided herein, e.g., containing dyes as disclosed herein, may advantageously maintain visibility for longer periods of time.

The product, where $R^1$, $R^2$, $R^3$ and $R^4$ are believed to be all or substantially all methyl, when subjected to thin-layer chromatography on silica developed with aqueous methanol (methanol:water 1:1) had a retention factor ($R_f$) of 0.83, while the starting material had an $R_f$ of 0.96. FIG. 1 shows the UV/Vis spectra of the product and the starting material (from an HP 8452A Diode Array Spectrophotometer). The methylated product was blue shifted from $\lambda_{max}$=600 nm for the starting material (CAS No. 314-13-6, as shown by line 102) to $\lambda_{max}$=588 nm (as shown by line 104). The product, like the starting material, was soluble in water and dimethyl sulfoxide, and slightly soluble in ethanol.

The product may be used, for example, for marking tissues of a patient during or in preparation for a surgical procedure. Such marking may be of external tissue (e.g., skin), or of internal tissues. For example, the product may be contained in an instrument, such as a surgical marker, for selectively dispensing a controlled amount of the product as desired to mark tissues.

Figure 2:
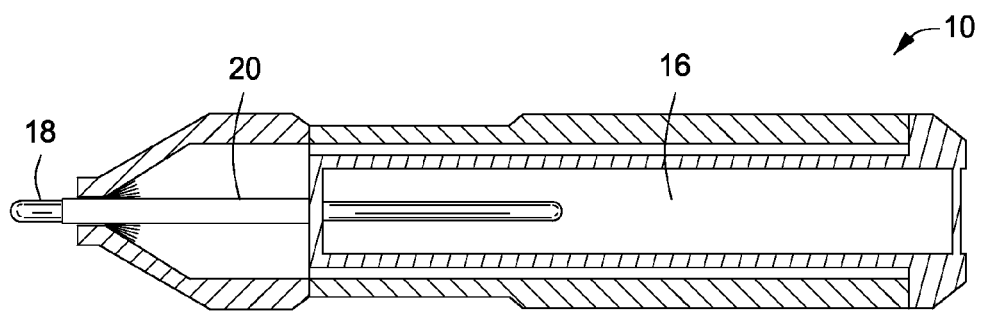
FIG. 2 depicts a pen for marking a patient in accordance with some embodiments of the present invention.

For example, FIG. 2 depicts an illustrative pen 10 for marking a patient, such as a human or other animal. The pen 10 may include a reservoir 16, a dispenser 18 (such as felt) for dispensing ink, and conduit 20 for fluid connection to the reservoir 16. The pen shown in FIG. 2 is illustrative only, and any other marking instrument suitable for us in marking a patient with compositions as taught herein may be utilized.

Figure 3:
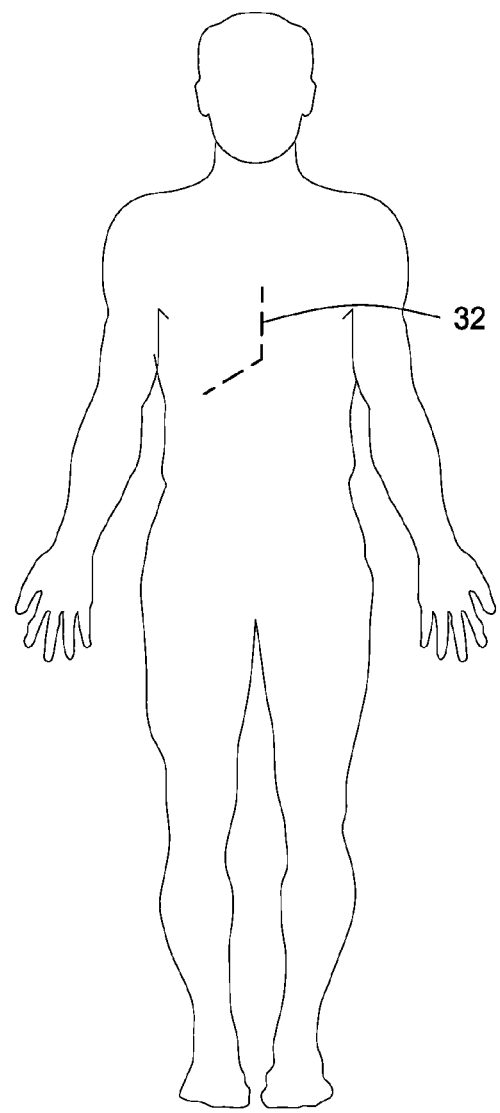
FIG. 3 illustrates a patient having markings made thereon in accordance with some embodiments of the present invention.

The inks can be used, for example, to mark the correct site or other body part to be operated upon. It can be used to mark the incision points and lines. Such markings are useful in error prevention protocols, such as a verbal check list answered by the professionals involved in a surgical operation. As illustrated in FIG. 3, a prospective course of incisions may be traced with dashed line 32.

The inks can be used, for example, to mark internal tissues and bone. The inks can be used, for example, to stain tissues and like samples in-vitro. Without being bound by theory, it is believed that the effective tissue staining is due to the dye binding to albumin. Skin marking is another illustrative application. The addition of alkyl(s) to CAS No. 314-13-6 can be useful for tuning leach/penetration rates and/or solubility in the solvent carrier.

Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A dye composition comprising one or more dyes of formula II:

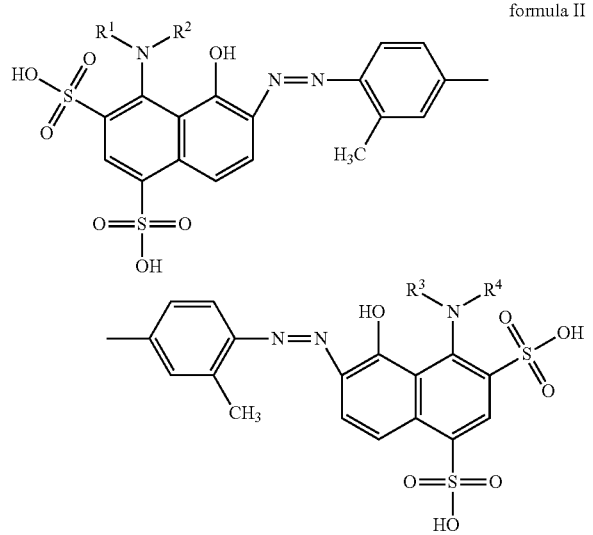

formula II wherein $R^1$, $R^2$, $R^3$ and $R^4$ are independently H or alkyl, so long as one or more is alkyl, and salts of the compound of formula II, wherein the dye composition is configured to provide coloring to an ink composition, with said ink composition having blue coloring due to said one or more dyes.

2. A dye composition of claim 1, wherein alkyl of $R^1$, $R^2$, $R^3$ or $R^4$ is C1-C4 alkyl.
3. A dye composition of claim 2, wherein one or more alkyls of $R^1$, $R^2$, $R^3$ or $R^4$ is attached via a primary carbon.
4. An ink comprising the dye composition of claim 1.
5. An ink comprising the dye composition of claim 2.
6. An ink comprising the dye composition of claim 3.
7. A method of synthesizing a dye of formula IIa:

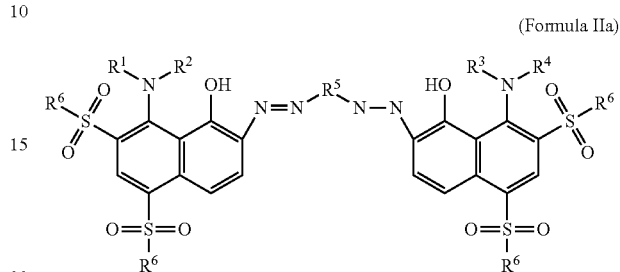

(Formula IIa)

wherein $R^5$ is

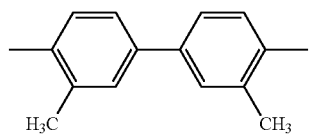

$R^1$, $R^2$, $R^3$ and $R^4$ are independently H or alkyl, so long as one or more is alkyl,
and wherein $R^6$ represents —O⁻M⁺, where M⁺ is a cation, the method comprising:
contacting a compound of formula IV

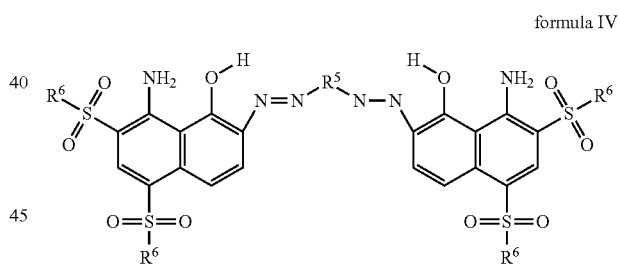

formula IV with R—X, wherein R is alkyl and X is a leaving group; and
obtaining the compound of Formula IIa.

8. The method of claim 7, wherein alkyl of $R^1$, $R^2$, $R^3$ or $R^4$ is C1-C4 alkyl.
9. The method of claim 8, wherein one or more alkyls of $R^1$, $R^2$, $R^3$ or $R^4$ is attached via a primary carbon.
10. A surgical marker containing the dye composition of claim 1.
11. A surgical marker containing the dye composition of claim 2.
12. A surgical marker containing the dye composition of claim 3.
13. An apparatus for marking patients, comprising:
an ink reservoir;
an ink dispenser having a fluid connection to the ink reservoir to dispense the ink at a desired rate to mark a patient; and
an ink disposed in the ink reservoir, the ink comprising a dye of formula II:

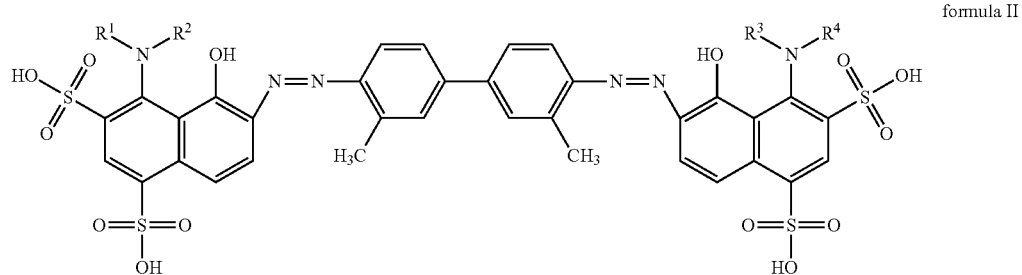

formula II formula II wherein $R^1$, $R^2$, $R^3$ and $R^4$ are independently H or alkyl, so long as one or more is alkyl, and salts of the compound of formula II.

14. An apparatus for marking patients of claim 13, wherein alkyl of $R^1$, $R^2$, $R^3$ or $R^4$ is C1-C4 alkyl.

15. An apparatus for marking patients of claim 14, wherein one or more alkyls of $R^1$, $R^2$, $R^3$ or $R^4$ is attached via a primary carbon.

16. A method of marking a patient, comprising:
determining a portion of a patient to be marked; and
applying an ink to the patient to mark the portion of the patient, the ink comprising the dye composition described in claim 1.

17. A method of marking a patient, comprising:
determining a portion of a patient to be marked; and
applying an ink to the patient to mark the portion of the patient, the ink comprising the dye composition described in claim 2.

18. A method of marking a patient, comprising:
determining a portion of a patient to be marked; and
applying an ink to the patient to mark the portion of the patient, the ink comprising the dye composition described in claim 3.

19. The dye composition of claim 1, wherein the composition is essentially free of carbon black.

20. The apparatus of claim 13, wherein the apparatus is configured to provide blue coloring to a surgical patient due to said dye.

* * * * *